(12) United States Patent
Dumas et al.

(10) Patent No.: US 7,060,693 B1
(45) Date of Patent: Jun. 13, 2006

(54) *AJUGA TURKESTANICA* EXTRACT AND ITS COSMETIC USES

(75) Inventors: Marc Dumas, Orleans (FR); Frédéric Bonte, Orleans (FR); Catherine Gondran, St Benoit-sur-Loire (FR)

(73) Assignee: LVMH Recherche, Paris (FR)

( * ) Notice: Subject to any disclaimer, the term of this patent is extended or adjusted under 35 U.S.C. 154(b) by 69 days.

(21) Appl. No.: 10/130,788

(22) PCT Filed: Nov. 24, 2000

(86) PCT No.: PCT/FR00/03274

§ 371 (c)(1),
(2), (4) Date: May 23, 2002

(87) PCT Pub. No.: WO01/37799

PCT Pub. Date: May 31, 2001

(30) Foreign Application Priority Data

Nov. 26, 1999 (FR) .................................. 99 14893

(51) Int. Cl.
*A61K 31/56* (2006.01)

(52) U.S. Cl. ...................................... 514/170; 514/171
(58) Field of Classification Search ................ 514/170, 514/171
See application file for complete search history.

(56) References Cited

U.S. PATENT DOCUMENTS

| 3,527,777 | A | | 9/1970 | Jizba et al. | |
| 5,198,225 | A | | 3/1993 | Meybeck et al. | |
| 5,609,873 | A | * | 3/1997 | Meybeck et al. | ............ 424/763 |
| 5,882,664 | A | * | 3/1999 | Soma et al. | ................. 424/401 |

FOREIGN PATENT DOCUMENTS

| EP | 0 440 494 | | 8/1991 |
| EP | 0440494 | * | 8/1991 |
| EP | 0 740 930 A1 | | 11/1996 |
| FR | 2 696 075 | | 4/1994 |
| JP | 7-316057 | | 12/1995 |
| WO | WO 94/04132 | * | 3/1994 |

OTHER PUBLICATIONS

Mamatkhanov et al., "Isolation of Turkesterone from the Epigeal Part of Ajuga Turkestanica and its Anabolic Activity.", Chemistry of Natural Compounds, vol. 34(2), pp. 150-154, 1998.*

Syrov et al., "Effect of a lipid concentrate from the aboveground portion of Ajug turkestanica on the metabolic proceses and dynamics of healing skin wounds experimentally". Pharmaceutical Chem. J., vol. 28(11), pp. 837-840, 1994.*

Mamatkhanov, A.U., et al., "Isolation of Turkesterone from the Epigeal Part of *Ajuga turkestanica* and its Anabolic Activity". Chem. Nat. Compd., vol. 34, No. 2, pp. 150-154, (1998).

Kotenko, L.D., et al., "Monitoring of Total Iridoid Production by Ajuga Turkestanica". Chemical Abstracts Service, vol. 123, No. 296372, (1994).

Syrov, V. N., et al., "Effect of a lipid concentrate from the aboveground portion of *Ajuga turkestanica* on the metabolic processes and dynamics of healing skin wounds experimentally." Pharmaceutical Chemistry Journal , vol. 28, No. 11, pp. 837-840, 1994.

Jung, Jin Sup, et al., "Molecular Structure of the Water Channel through Aquaporin CHIP". J. Biol. Chem., vol. 269, No. 20, pp. 14648-14654, 1994.

Sougrat, R., et al., "Functional expression of AQP3 in human epidermis and keratinocyte cultures". Molecular Biology of the Cell, vol. 9, p. 499a, 1998 (abstract only).

* cited by examiner

*Primary Examiner*—Barbara P. Badio
(74) *Attorney, Agent, or Firm*—Nath & Associates PLLC; Gary M Nath; Tanya Harkins

(57) ABSTRACT

The invention relates to an extract of the plant *Ajuga turkestanica* containing at least one ecdysteroid and at least one iridoid and obtainable by extraction of at least part of said plant by means of a solvent or solvent mixture consisting of 0 to 60% by weight of water, the remainder of said solvent or solvent mixture consisting of at least one $C_1$ to $C_4$ alcohol and/or acetone and/or butylene glycol and/or propylene glycol, and very particularly to an extract containing one part by weight of ecdysteroids to 2 to 4 parts by weight of iridoids.

The invention further relates to cosmetic uses of these extracts or associations containing one part by weight of ecdysteroids to 2 to 4 parts by weight of iridoids as cosmetic agents for improving the differentiation of keratinocytes, for regulating the water fluxes and the water absorption in the epidermis or for hydrating the epidermis.

The invention further relates to a method of cosmetic skin treatment in which a cosmetically effective amount of the extracts or associations defined above is applied.

22 Claims, No Drawings

AJUGA TURKESTANICA EXTRACT AND ITS COSMETIC USES

This application is a 371 of PCT/FR00/03274 filed Nov. 24, 2000.

The present invention relates to a novel extract of the plant *Ajuga turkestanica* and to its applications in the field of cosmetics.

French patent FR 2 696 075 has described the use of ecdysteroids for strengthening the skin's water barrier through their action on the differentiation of keratinocytes. Said patent cites a large number of both animal and vegetable sources of ecdysteroids. In particular, these numerous sources include two plants of the *Ajuga* family, namely *Ajuga iva* and *Ajuga decumbens*.

The plant *Ajuga turkestanica* is a plant of the Labiae family, of the genus *Ajuga* and species *turkestanica*, which grows in central Asia, particularly in Ouzbekistan. Its traditional Ouzbek name is "sanobar" or "the charmer".

This plant was used in traditional medicine in the form of an infusion for its toning and liver-protecting properties.

A recent study entitled "Effect of a lipid concentrate from the aboveground portion of *Ajuga turkestanica* on the metabolic processes and dynamics of healing skin wounds experimentally", Pharmaceutical Chemistry Journal, vol. 28, no. 11, 1994, 837–840, reported pharmacological tests performed on chloroform extracts of the aerial parts of this plant. The results reported in said publication revealed that the extracts possessed a certain tissue-hydrating activity.

The inventors of the present invention have now discovered that, if solvents are used which are appreciably more polar than those used within the framework of said experimental study, it is possible to obtain very different extracts possessing remarkably improved epidermis-hydrating properties associated not only with an improvement in the differentiation of keratinocytes, leading to a strengthening of the skin's water barrier, but also with a so-called "active hydration" of the epidermis by water absorption and an improvement in the water fluxes in the epidermis.

The extracts, which in themselves are novel products, form the first subject of the present invention, which, according to other subjects, further relates to cosmetic compositions and to uses of these extracts in the field of cosmetics.

Furthermore, while pursuing their researches, the inventors of the present invention demonstrated that some of the extracts of the invention contained associations of well-defined active ingredients in well-defined proportions, hereafter referred to as "associations" of the invention, which have so far never been used in cosmetic compositions. The cosmetic compositions containing these associations, and the cosmetic uses of these associations, therefore form another subject of the invention.

The inventors of the present invention deduced, from the properties of the extracts and associations of the invention, that these extracts and associations were particularly active in regulating and/or improving the functionality of aquaporins AQP3.

Aquaporins, or water channels, are transmembrane protein systems for transporting water and small molecules, for example glycerol and urea, in solution. These aquaporins have a size of about 30 kDa with 6 transmembrane passages in an alpha helix (Jung et al., "Molecular structure of the water channel through aquaporin CHIP" in J. Biol. Chem., 1994, vol. 269, pp. 14648–14654).

The presence of type 3 aquaporins, or AQP3, in the human epidermis, and more precisely in the plasmic membrane of human skin keratinocytes, was described by R. SOUGRAT et al. in an article entitled "Functional expression of AQP3 in human epidermis and keratinocyte cell cultures", published in Molecular Biology of the Cell, November 1998, vol. 9, page 499a. In this article, R. SOUGRAT et al. also described the important role played by these AQP3 in the water transport within the human epidermis.

Thus the invention results from the discovery that, by selecting particularly polar solvent media, it is possible to obtain extracts of the plant *Ajuga turkestanica* which possess particularly valuable cosmetic properties, and that some of these extracts contain associations of active ingredients whose cosmetic use affords the same remarkable cosmetic properties. In particular, these extracts and associations make it possible to improve the differentiation of keratinocytes, which in turn makes it possible to improve the hydration of the skin and obtain a particularly effective anti-ageing activity. Furthermore, the inventors of the present invention have observed that the extracts and associations of the invention are particularly effective in regulating the water fluxes in the epidermis, an activity which they have been able to relate to a remarkable activity of the extracts of the invention in the regulation and/or functionality of aquaporins AQP3, thereby affording a better hydration of the basal layers of the epidermis.

Thus, according to one of its essential characteristics, the invention relates to an extract of the plant *Ajuga turkestanica*, characterized in that it contains at least one ecdysteroid and at least one iridoid and in that it is obtainable by extraction of at least part of said plant by means of a solvent or solvent mixture consisting of 0 to 60% by weight of water, the remainder of said solvent or solvent mixture consisting of at least one $C_1$ to $C_4$ alcohol and/or acetone and/or butylene glycol and/or propylene glycol.

The extraction process which can be used to prepare the extracts of the invention is advantageously carried out under conditions such that said extraction is performed with said solvent or solvent mixture for 1 to 4 hours.

The extraction process which can be used to prepare the extracts of the invention is advantageously carried out under conditions such that said extraction is performed at the reflux temperature of said solvent or solvent mixture for 1 to 4 hours.

The extraction can be performed on the whole plant or on part of the plant. However, the extracts of the invention will preferably be prepared using the roots of the plant.

The proportions of water and alcohol or water and acetone in the solvent or solvent mixture used to carry out the extraction process for preparing the extracts of the invention can vary within wide limits. However, for the alcoholic solvents or acetone, the water will preferably be in a proportion of between 0 and 50% by weight.

The proportions of water and butylene glycol or propylene glycol in the solvent or solvent mixture used to carry out the extraction process for preparing the extracts of the invention can vary within wide limits. However, for butylene glycol or propylene glycol, the water will preferably be in a proportion close to 50% by weight.

The solvent mixture used to carry out the extraction process for preparing the extracts of the invention can be composed of any mixture of $C_1$ to $C_4$ alcohols, water, butylene glycol and propylene glycol.

Essentially methanol and ethanol may be mentioned as preferred alcohols for carrying out the process for preparing the extracts of the invention.

The extracts according to the invention will advantageously be prepared using water/ethanol, water/methanol, water/acetone, water/propylene glycol or water/butylene glycol mixtures.

In the case of the water/ethanol mixtures, the chosen mixture will advantageously contain 70 to 90% of ethanol and 30 to 10% of water, preferably 80% of ethanol to 20% of water.

In the case of the water/methanol mixtures, the chosen mixture will advantageously contain 70 to 90% of methanol and 30 to 10% of water, preferably 80% of methanol to 20% of water.

In the case of the water/acetone mixtures, the chosen mixture will advantageously contain 70 to 90% of acetone and 30 to 10% of water, preferably 80% of acetone to 20% of water.

In the case of the water/propylene glycol mixtures, the chosen mixture will advantageously contain 40 to 60% of propylene glycol and 60 to 40% of water, preferably 50% of propylene glycol to 50% of water.

In the case of the water/butylene glycol mixtures, the chosen mixture will advantageously contain 40 to 60% of butylene glycol and 60 to 40% of water, preferably 50% of butylene glycol to 50% of water.

It has been found that the extracts of the invention advantageously contain associations comprising one part by weight of at least one ecdysteroid and 2 to 4 parts by weight, preferably 3 parts by weight, of at least one iridoid.

For the sake of simplicity, these associations are hereafter referred to as "associations" according to the invention.

In one advantageous variant, the ecdysteroids contained in these associations are preferably selected from the group comprising ecdysterone, ecdysterone 2,3-monoacetonide, turkesterone, cyasterone, 22-acetylcyasterone and alpha-ecdysone.

In another advantageous variant, the iridoids contained in these associations are selected from the group comprising harpagide and its 8-O-acetyl derivative.

In one advantageous variant, the different ecdysteroids contained in these associations are composed of 30 to 35% of ecdysterone, 20 to 25% of turkesterone, 20 to 24% of 22-acetylcyasterone, 11 to 15% of ecdysterone 2,3-monoacetonide, 6 to 7% of alpha-ecdysone and 2 to 4% of cyasterone, the percentages being expressed by weight.

In another advantageous variant, the iridoids are composed of 60 to 70% of 8-O-acetylharpagide and 30 to 40% of harpagide, the percentages being expressed by weight.

As explained previously, the extracts of the invention have a particular activity in the differentiation of keratinocytes, enabling them to contribute to a strengthening of the role of the epidermis as a water barrier, thereby improving its hydration and playing an anti-ageing role, and improving the appearance and quality of the skin to give an attractive, soft skin.

The tests performed by the inventors of the present invention have shown that the remarkable properties of the extracts of the invention are also obtained with the specific associations of ecdysteroid and iridoid defined above.

Thus, according to a second feature, the present invention relates to the use of an extract of the plant *Ajuga turkestanica*, or an association of at least one ecdysteroid and at least one iridoid as defined above, as a cosmetic agent for improving the differentiation of keratinocytes. This activity in the differentiation of keratinocytes has the effect of improving the function of the epidermis as a water barrier and consequently leads to a hydrating effect and an anti-ageing effect, and also makes it possible to improve the appearance and quality of the skin to give, in particular, an attractive, softer skin.

As explained previously, the tests performed by the inventors have made it possible to demonstrate the activity of the extracts of the invention and the associations defined above in the water transport in the epidermis, said activity being at least partly related to an action, also demonstrated by the inventors of the invention, on the regulation and/or functionality of aquaporins AQP3.

In fact, it is well known that, as skin ages, it becomes thinner and drier to give the thin, scaly appearance found particularly in the elderly. It is well known that there is a water gradient in the skin from the basal layer of the epidermis to the more superficial layers of the stratum corneum. Now, after having studied the water transport on treated and control emersed cultures of normal human keratinocytes, the inventors of the present invention used permeability measurements to demonstrate that the extracts of the invention made it possible to increase the water fluxes in the epidermis and especially the water absorption fluxes towards the basal layer of the epidermis, leading to a better hydration of the epidermis and particularly the basal layers of the epidermis.

Other studies carried out by the inventors of the present invention have also made it possible to demonstrate the effect on aquaporins AQP3.

Thus, according to another feature, the invention relates to the use of the extracts of the invention and the associations as defined above as cosmetic agents for regulating the water fluxes and water absorption in the epidermis.

According to yet another feature, the invention relates to the use of these extracts or associations as cosmetic agents for hydrating the epidermis.

According to a fifth feature, the invention further relates to a cosmetic composition, especially with activity in the differentiation of keratinocytes, which improves the function of the epidermis as a water barrier and has a hydrating effect and an anti-ageing effect, said composition being intended to improve the appearance and quality of the skin and to improve its hydration by regulation of the water fluxes and the water absorption in the epidermis, characterized in that it contains a cosmetically effective amount, for the intended purpose, of an extract of the plant *Ajuga turkestanica* as defined above or an association as defined above.

The proportion of extract of the plant *Ajuga turkestanica* is preferably between 0.005 and 10% by weight, particularly preferably between 0.01 and 2% by weight, based on the total weight of the composition.

Furthermore, the extract of the plant *Ajuga turkestanica* according to the present invention is advantageously used in the compositions of the invention in combination with any other active principle known to those skilled in the art, particularly with any other active principle selected from the group comprising vitamin A and its esters, particularly vitamin A palmitate and acetate, vitamin E and its esters, particularly vitamin E phosphate and acetate, vitamin C and its derivatives, particularly magnesium ascorbylphosphate, xanthines, particularly caffeine, asiatic acid, madecassic acid, asiaticosides, madecassosides, extracts of *Centella asiatica*, ellagic acid, soya saponins, extracts of *Bertholletia*, extracts of *Panax Ginseng*, pure sea water, magnesium aspartate, manganese chloride, cyclic AMP, D-xylose, hyaluronic acid, calcium gluconate, isoflavones, ammonium glycyrrhizinate, corticosteroids, extracts of *Phellodendron amurense*, resveratrol and piceids.

The isoflavones mentioned above are especially those marketed under the name "fujiflavones" by the Japanese company FUJICCO.

In general, the cosmetic compositions of the invention contain cosmetically acceptable excipients or carriers for topical application to the skin. Examples of such cosmetically acceptable excipients or carriers are well known to those skilled in the art.

The compositions of the invention can be formulated in any cosmetically acceptable form, particularly in the form of a cream, gel or lotion.

The invention further relates to a method of cosmetic skin treatment in which a cosmetically effective amount of an extract according to the invention or an association as defined above is applied to the skin.

It can be seen that the invention thus makes it possible to put into effect the particularly unexpected properties observed for the extract of the plant *Ajuga turkestanica*.

Other objects, characteristics and advantages of the invention will become clearly apparent to those skilled in the art from the following explanatory description referring to a test of activity in the improvement and the differentiation of keratinocytes and to a test for demonstrating the water transport in the epidermis. Various Examples of formulations of cosmetic compositions are also given simply by way of illustration and cannot therefore in any way limit the scope of the invention. All the percentages in the Examples are given by weight, unless indicated otherwise.

EXAMPLES

A—Preparation of an Extract According to the Invention

Roots of *Ajuga turkestanica* are extracted hot with a solvent composed of 80% of ethanol and 20% of water.

10 kg of dry matter (roots of *Ajuga turkestanica*) are subjected to the action of 160 kg of solvent (ethanol/water mixture in respective proportions of 80/20) at 50° C. for 2 hours.

The resulting mixture is cooled to room temperature (about 21° C.).

The cooled mixture is then filtered on a 5 μm filter (to remove the suspended and precipitated matter).

The filtered mixture is evaporated to dryness (to remove the extraction solvent).

The mixture which has been evaporated to dryness is taken up in 1 liter of water.

The mixture which has been taken up in 1 liter of water is subjected to vigorous homogenization (by agitation) plus ultrasound. This treatment (homogenization+ultrasound) is continued until a homogeneous solution is obtained.

The homogenized mixture is frozen rapidly to −40° C. and kept at this temperature for about 4 hours.

The frozen mixture is lyophilized.

The powder obtained after lyophilization is a dry extract of *Ajuga turkestanica* according to the invention, which will be called "extract S".

This extract was analyzed using the conventional analytical techniques, especially:

use of specific developers for reaction chemistry
high performance liquid chromatography (HPLC)
high performance thin layer chromatography (HPTLC)
gas chromatography (GC)

and corresponds to the composition given below in percentages by weight:

ecdysterone . . . 2.75%
turkesterone . . . 2.00%
22-acetylcyasterone . . . 1.93%
ecdysterone 2,3-monoacetonide . . . 1.18%
alpha-ecdysone . . . 0.59%
cyasterone . . . 0.27%
ajugasterone B . . . 0.028%
ajugalactone . . . 0.016%
8-O-acetylharpagide . . . 16.70%
harpagide . . . 9.20%
pectinic substances . . . 24.30%
tannins . . . 4.92%
water . . . 6.95%
monosaccharides (fructose, glucose) . . . 19.98%
ash . . . 6.97%

This extract can be incorporated into cosmetic compositions.

It is of course possible to improve this extract by subjecting it to purifications, for example in order to remove the tannins, the polysaccharides, the polypeptides and the chlorophyll pigments. Numerous techniques are available to those skilled in the art for carrying out these purifications; examples which may be mentioned are the use of selective absorbents such as active charcoal or silica gels, differential precipitation techniques, differential solubilization techniques or liquid—liquid partition techniques.

For the purposes of Examples B, C and D below, this powder ("extract S") is redissolved to give a solution containing 25% of powder, 25% of water and 50% of ethanol, based on the total weight of the final solution. The solution obtained will be called "extract L".

B—Demonstration of the Activity of the Extract of the Invention in the Differentiation of Normal Human Keratinocytes This experiment is carried out using the root extract of the plant *Ajuga turkestanica* obtained according to Example A ("extract L").

The present experiment uses this extract to measure the differentiation of normal human keratinocytes in emersed cell culture.

Within the framework of the invention, the differentiation of keratinocytes is understood as meaning all the phenomena involved in the maturation of keratinocytes into corneocytes.

To do this, emersed cell cultures of human keratinocytes treated with the extract according to the invention were compared with untreated cultures according to morphological criteria by optical or electron microscopy techniques.

The more specific conditions of the experiment are now described below.

a) Preparation of Cultures of Normal Human Keratinocytes, Abbreviated to NHK

Normal human keratinocytes, or NHK, were obtained from mammaplasty skin of a 29-year-old white woman by the method described by Eisinger M. in an article entitled "Cultivation of normal human epidermal keratinocytes and melanocytes" in the book "Methods in skin research" published by D. SKERROW and C. J. SKERROW, 1985, pp. 191–212. These NHK, cultivated in SFMc medium from Gibco, were used to prepare reconstructed epidermides, on which the extract according to the invention is tested.

b) Preparation of Reconstructed Epidermides

Insert emersion culture is a technique described in the literature, in particular by M. S. NOEL-HUDSON et al. in the article entitled "Human epidermis reconstructed on synthetic membrane: Influence of experimental conditions on terminal differentiation" in the journal In Vitro Cell. Dev. Biol., 1995, 31, pp. 508–515.

The cultures are carried out in a system comprising two compartments (upper/lower) with the aid of COSTAR plates containing 12 wells marketed by D. DUTSCHER, inside which COSTAR Transwell-clear inserts of diameter 12 mm, also marketed by DUTSCHER, are placed.

The NHK are inoculated onto Transwell-clear inserts at a rate of 115,000 NHK per insert and cultivated in immersion culture in SFMc medium to the point of confluence, the culture medium being added to the upper compartment.

At the point of confluence of the NHK, the SFMc medium is removed from the upper compartment and the extract of the plant *Ajuga turkestanica* according to the present invention is then added to the differentiation medium, after which the latter is added to the lower compartment to give an emersion culture at the air/liquid interface.

The differentiation medium has the following essential composition:

DMEM: HAM's F12 from Gibco, containing 5% of fetal calf serum, also from Gibco.

The extract according to the invention ("extract L" described in Example A) was conditioned in stock solution at a concentration of 25 mg/ml in DMSO (dimethyl sulfoxide) and filtered on Millex FGS sterilizing filters of porosity 0.22 µm. The product is then brought into contact with the cultures as soon as they have been emersed, at concentrations of 2.5, 10 and 25 µg/ml in the differentiation medium, for 14 days, with renewal every 48–72 h. Three experiments were performed for each test concentration.

The control cultures received the same proportion of DMSO as the treated cultures, i.e. 0.1% v/v, the frequency of medium changes and the duration of the treatment being identical to those of the treated cultures.

c) Treatment of the Cultures for Microscopic Analysis

After 14 days of treatment with the extract according to the invention ("extract L"), the reconstructed epidermides are treated so that they can be observed by electron and optical microscopy, making it possible to carry out an ultrastructural study of the differentiation of keratinocytes in these reconstructed epidermides.

To do this, the emersed cell cultures are successively subjected to tissue fixation with glutaraldehyde, dehydration with ethanol and inclusion in resin, for example by the method described by A. R. SPURR in J. Ultrastruct. Res. USA, 1969, 26, pp. 31–43, and entitled "A low-viscosity epoxy resin embedding medium for electron microscopy".

Semi-thin sections are then produced for observation by optical microscopy and ultra-thin sections for observation by electron microscopy.

d) Observations

In optical microscopy, the semi-thin sections stained with toluidine blue revealed that the thickness of the layers of corneocytes constituting the corneal layer—or stratum corneum—of the epidermis had increased very considerably in the reconstituted epidermides treated with the extract according to the invention, compared with the control reconstituted epidermides. The thickness increases by a factor of about 3 to 4, depending on the culture.

In reality, it was observed that the stratum corneum of the control emersed cell cultures was greatly reduced, whereas the treatment with the extract of the plant *Ajuga turkestanica* according to the invention made it possible to restore the corneal layer of normal thickness.

As the total thickness of the culture is the same in both cases, it can be observed that there are more layers of basal and suprabasal keratinocytes in the case of the control culture. This is an effect of the extract of the invention on the differentiation of keratinocytes. It is precisely at the interface between the last suprabasal layer of keratinocytes and the first layer of corneocytes of the stratum corneum that the observations reported below are then made by transmission electron microscopy.

Furthermore, in the case of the emersed cell cultures treated with the extract according to the invention at doses of 10 µg/ml and 25 µg/ml, the same type of keratinocyte differentiation profile is observed, clearly showing a uniformity between all the treated cultures compared with the control culture, which is really very different. In addition, as regards the observations made by transmission electron microscopy at the interface between the suprabasal layers (HK) and the stratum corneum (CO) using the ultra-thin sections contrasted with uranyl acetate and lead citrate, the advance in the differentiation of keratinocytes can be appreciated in the following manner:

a) Control emersed cell culture at 30,000× magnification:
relatively few desmosomes
weakly differentiated desmosomes
relatively poorly visible corneal envelope
thick corneocytes
diffuse keratin network
no visible corneodesmosomes b) For the emersed cell cultures treated with the extract according to the invention at respective doses of 2.5, 10 and 25 µg/ml, the same observations can be made:
large number of desmosomes
very well differentiated desmosomes
keratin filaments joined to the desmosomal plate
keratin filaments oriented parallel to the corneocytes
clearly visible corneal envelope on the HK side
relatively thin corneocytes
compact keratin network
presence of corneodesmosomes
observable intercorneocyte space (lipid)

It can be concluded from these experiments that the extracts according to the invention appear to be extremely active at low doses. In the experiments performed, the extract according to the invention is active at or above a concentration of 2.5 µg/ml on the intercellular cohesion specifically at one of the key layers of the epidermis, at the interface between the corneal layer and the basal layers.

The novel character of this extract is such that it optimizes the bond between the living layers and the corneal layer, which had not been observed hitherto in vitro.

With the extract according to the invention, the keratin filaments are better organized and bonded to the desmosomal plates. This strongly suggests that, by virtue of an excellent local elasticity, the corneal layer can undergo local deformations (associated with the physical stresses it receives) without suffering damage. In addition, the general effect of the extract of the invention on the formation of a corneal layer of good quality, by virtue of obtaining relatively thin corneocytes with a clearly visible corneal envelope and a compact keratin network, makes it possible to envisage a regulatory action on the hydration of the superficial layers of the epidermis.

Thus the extracts of the invention will make it possible to strengthen the role of the epidermis as a water barrier and to improve the condition of the epidermis and hence the appearance and quality of the skin, which will be attractive and soft. By virtue of its keratinocyte-differentiating effect, the invention provides a particularly valuable anti-ageing effect.

C—Demonstration of the Effect of an Extract of the Invention on the Water Transport in the Skin The keratinocyte cultures are prepared from second-passage keratinocytes originating from a plasty performed on a 21-year-old woman, on a Costar Transwell membrane of porosity 3 μm in a keratinocyte differentiation medium such as that described by M. S. NOEL-HUDSON et al. in the article entitled "Human epidermis reconstructed on synthetic membrane: Influence of experimental conditions on terminal differentiation" in the journal In Vitro Cell. Dev. Biol., 1995, 31, pp. 508–515.

The cells were treated with the extract according to the invention ("extract L" as described in Example A) at a concentration of 2.5 μg/ml for 6 and 17 days, with renewal of the medium every 2–3 days, the extract according to the invention being solubilized in DMSO at a concentration of 10 mg/ml and diluted to 1/4000 immediately before use. The control cells receive the same amount of DMSO.

D0 is understood as meaning the day on which the cultures which have reached confluence are emersed from their culture medium and exposed to the air.

The permeability measurements were made on D=0, D=6 and D=17 according to a protocol described by R. A. Dorr et al. in "A new data-acquisition system for the measurement of the net water flux across epithelia", Computer Methods and Programs in Biomedicine, 1997, 53, pp. 9–14.

To make the permeability measurements, the filters are placed in a measuring chamber composed of two compartments filled with culture medium. The luminal compartment (upper part of the culture) is closed with a catheter connected to a horizontal capillary tube filled with dye. Any movement of liquid results in a displacement of the dye, which can be measured. The water flux will be measured in the absence of an osmotic gradient (isotonicity in both media). The water flux measured is the consequence of a net flux of solution across the preparation. The permeability to water is measured in $\mu l/min/cm^2$.

At D=0 the cells do not present a significant barrier to the passage of water, as demonstrated by a massive absorption of water when a hydrostatic pressure is applied to the luminal compartment. After D0 the cells differentiate progressively into multilayers and after D4 or D7, depending on the strains used, the cells develop a resistance to the passage of water.

The Table below gives the water fluxes in human epidermides of cultures treated with the extract according to the invention ("extract L" as described in Example A) at a concentration of 2.5 μg/ml. The fluxes are expressed in $\mu l/min/cm^2$.

| Treatment time in days | Control epidermides $\mu l/min/cm^2$ | Treated epidermides $\mu l/min/cm^2$ |
|---|---|---|
| D6 | −0.49 | 0.76 |
| D17 | −0.015 | 0.12 |

A negative value indicates a secretion and a positive value indicates an absorption flux. In contrast to the control cells, for which a secretion of water is measured, the cells treated with the extract of *Ajuga turkestanica* according to the invention absorb a substantial amount of water. The magnitude of this absorption decreases at D=17, but remains very significant. The reason for this drop is the increase in the thickness of the epidermides and the formation of the stratum corneum and its impermeability to water. The water fluxes are therefore reduced. This is also true for the control cultures, but to a lesser extent.

CONCLUSION

The present study demonstrates that the product described in Example A ("extract L"), used at a concentration of 2.5 μg/ml under the conditions mentioned above, strongly favors a water absorption phenomenon. The flux moves towards the germinative keratinocyte layers and favors their hydration. This water absorption makes it possible to increase or maintain the hydration of the "living" layers (keratinocytes) of the epidermis which are located under the corneal layer of the epidermis.

D—Demonstration of the Action of an Extract of the Invention on the Functionality of Aquaporins AQP3

In an article entitled "Functional expression of AQP3 in human epidermis and keratinocyte cell cultures" published in Molecular Biology of the Cell, November 1998, vol. 9, page 499a, R. SOUGRAT et al. described the presence of aquaporins- 3 (AQP3) in the plasmic membrane of the keratinocytes of human skin. They also describe their important role in the water transport within the human epidermis.

It was shown in Example C that the extract according to the invention greatly increases the water absorption fluxes in the human epidermis. Taking into account the magnitude of the water fluxes measured, they can only be explained by a water transport controlled by AQP3. A transcellular passage across the phospholipidic bilayer of the plasmic membrane of the keratinocytes would be of much too small an amplitude. A check was made to rule out the possibility of a pericellular passage of water. In fact, when the hydrostatic pressure applied to the epidermis is varied, the water flux is not affected.

It is for this reason that the inventors of the present invention deduced that these extracts were particularly active in regulating and/or improving the functionality of aquaporins-3 (AQP3).

E—Cosmetic Compositions

The extracts of *Ajuga turkestanica* in the cosmetic compositions described below are dry extracts, unless indicated otherwise.

E1—Moisturizing Nourishing and Anti-Ageing Emulsion

| | |
|---|---|
| Extract of Ajuga turkestanica (extract S) | 0.025 g |
| Vitamin E acetate | 0.100 g |
| Vitamin A palmitate | 0.010 g |
| Magnesium ascorbylphosphate | 0.200 g |
| Wheat ceramides | 0.200 g |
| Wheat proteins | 1.000 g |
| UVA-UVB filter | 5.000 g |
| Excipient with preservatives and perfumes | qsp 100 g |

The extract of *Ajuga turkestanica* (extract S) used in this emulsion is the extract described above in Example A.

This nourishing emulsion improves the hydration of the skin, particularly the epidermis, refines the quality of the skin, improves its grain and reduces the wrinkles. It is applied daily to the face.

E2—Moisturizing, Firming and Restructuring Gel

| | |
|---|---|
| Extract of Ajuga turkestanica (extract S) | 0.040 g |
| Magnesium aspartate | 0.100 g |
| Extract of Centella asiatica | 0.100 g |
| Soya saponins | 0.050 g |
| Excipient with preservatives and perfumes | qsp 100 g |

The extract of *Ajuga turkestanica* (extract S) used in this gel is the extract described above in Example A.

This moisturizing gel exerts a toning effect on the skin and improves the suppleness and firmness. It is applied daily to the face, neck and bust.

E3—Moisturizing Liposomal Repair Gel

| | |
|---|---|
| Extract of Ajuga turkestanica (extract S) | 0.020 g |
| Soya lecithin | 2.000 g |
| Vitamin A acetate | 0.010 g |
| Vitamin E | 0.010 g |
| Excipient with preservatives and perfumes | qsp 100 g |

The extract of *Ajuga turkestanica* (extract S) used in this gel is the extract described above in Example A.

This liposomal gel is applied daily to the face, preferably in the evening. It improves the suppleness and hydration of the skin and favors its regeneration.

E4—Moisturizing and Toning Lotion

| | |
|---|---|
| Extract of Ajuga turkestanica (extract S) | 0.030 g |
| Marine spring water concentrated in trace elements | 10.000 g |
| Extract of Panax Ginseng | 0.200 g |
| Cyclic AMP | 0.010 g |
| Caffeine | 0.100 g |
| Excipient with preservatives and perfumes | qsp 100 g |

The extract of *Ajuga turkestanica* (extract S) used in this lotion is the extract described above in Example A.

This moisturizing lotion is applied daily to the face, preferably in the morning, to give a more attractive and more radiant skin.

E5—Moisturizing and Soothing Fluid

| | |
|---|---|
| Extract of Ajuga turkestanica | 0.04 g |
| Manganese chloride | 0.10 g |
| D-xylose | 0.10 g |
| Wheat ceramides | 0.20 g |
| Licorice extract | 0.10 g |
| Vitamin E acetate | 0.20 g |
| Excipient with preservatives and perfumes | qsp 100 g |

The extract of *Ajuga turkestanica* used in this fluid is obtained with a solvent composed of 80% of methanol and 20% of water. The extraction process is similar to that described in Example A except for the nature of the solvent mixture.

This fluid is used daily on the face and body as a topical application.

E6—Moisturizing Mascara

| | |
|---|---|
| Extract of Ajuga turkestanica | 0.025 g |
| Hyaluronic acid | 0.500 g |
| D-xylose | 0.200 g |
| Colored pigments | 10.000 g |
| Waxes | 30.000 g |
| Excipient with preservatives and perfumes | qsp 100 g |

The extract of *Ajuga turkestanica* used in this mascara is obtained with a solvent composed of 80% of acetone and 20% of water. The extraction process is similar to that described in Example A except for the nature of the solvent mixture.

E7—Rehydrating and Anti-Ageing After-Sun Patch

| | |
|---|---|
| Extract of Ajuga turkestanica | 0.5 g |
| Ammonium glycyrrhizinate | 0.5 g |
| Dextran sulfate | 0.2 g |
| Patch excipient | qsp 100 g |

The extract of *Ajuga turkestanica* used in this patch is obtained with a solvent composed of 50% of propylene glycol and 50% of water. The extraction process is similar to that described in Example A except for the nature of the solvent mixture.

E8—Antiseptic Moisturizing Cream for Chapping, Small Superficial Wounds and Redness Due to Irritation

| | |
|---|---|
| Extract of Ajuga turkestanica | 0.4 g |
| Extract of Phellodendron amurense | 0.1 g |
| Fusidic acid | 2.0 g |
| Excipient | qsp 100 g |

The extract of *Ajuga turkestanica* used in this cream is obtained with a solvent composed of 50% of butylene glycol and 50% of water. The extraction process is similar to that described in Example A except for the nature of the solvent mixture.

E9—Moisturizing, Nourishing and Anti-Ageing Emulsion

| | |
|---|---|
| Ecdysterone | 0.007 g |
| Turkesterone | 0.005 g |
| 22-Acetylcyasterone | 0.005 g |
| Ecdysterone 2,3-monoacetonide | 0.003 g |
| Alpha-ecdysone | 0.0015 g |
| Cyasterone | 0.0007 g |
| 8-O-acetylharpagide | 0.04 g |
| Harpagide | 0.02 g |
| Vitamin E acetate | 0.100 g |
| Vitamin A palmitate | 0.010 g |
| Magnesium ascorbylphosphate | 0.200 g |
| Wheat ceramides | 0.200 g |
| Wheat proteins | 1.000 g |
| UVA-UVB filter | 5.000 g |
| Excipient with preservatives and perfumes | qsp 100 g |

What is claimed is:

1. A method of hydration of the basal layers of the epidermis of a person having a deficiency in regulation of the water fluxes in the epidermis or having a deficiency in the functionality of aquaporins AQP3, comprising the topic application of an efficient amount of a cosmetic composition comprising at least one agent for regulation of water fluxes in the epidermis or for improving the functionality of aquaporins consisting essentially of a water alcoholic extract of *Ajuga turkestanica* containing one part by weight of at least one ecdysteroid, from 2 to 4 parts by weight of at least one iridoid in admixture with a cosmetically acceptable excipient or carrier for topical application to the skin.

2. The method according to claim 1, wherein said ecdysteroid is selected from the group consisting of ecdysterone, ecdysterone 2,3-monoacetonide, turkesterone, cyasterone, 22-acetylcyasterone and alpha-ecdysone.

3. The method according to claim 1, wherein said iridoid is selected from the group consisting of harpagide and its 8-O-acetyl derivative.

4. The method according to claim 1, wherein said ecdysteroids are composed of 30% to 35% of ecdysterone, 20% to 25% of turkesterone, 20% to 24% of 22-acetylcyasterone, 11% to 15% of ecdysterone 2,3-monoacetonide, 6% to 7% of alpha-ecdysone and 2% to 4% of cyasterone, the percentages being expressed by weight.

5. The method according to claim 1, wherein said iridoids are composed of 60% to 70% of 8-O-acetylharpagide and 30% to 40% of harpagide, the percentages being expressed by weight.

6. The method according to claim 1, wherein said extract is obtained by extraction of at least part of said plant by means of a solvent or solvent mixture consisting of 0% to 60% by weight of water, the remainder of said solvent or solvent mixture consisting of at least one $C_1$ to $C_4$ alcohol and/or acetone and/or butylenes glycol and/or propylene glycol.

7. The method according to claim 6, wherein said extraction is performed with said solvent or solvent mixture for 1 to 4 hours.

8. The method according to claim 6, wherein said extraction is performed at the reflux temperature of said solvent or solvent mixture for 1 to 4 hours.

9. The method according to claim 6, wherein said extraction is performed on the whole of said plant.

10. The method according to claim 6, wherein said extraction is performed on the roots of said plant.

11. The method according to claim 6, wherein said solvent mixture is a mixture of water and ethanol.

12. The method according to claim 11, wherein the mixture of water and ethanol is a mixture containing 70% to 90% ethanol and 10% to 30% water.

13. The method according to claim 6, wherein said solvent or solvent mixture is a mixture of water and methanol.

14. The method according to claim 13, wherein said mixture of water and methanol is a mixture containing 70% to 90% methanol and 10% to 30% water.

15. The method according to claim 6, wherein said solvent or solvent mixture is a mixture of water and acetone.

16. The method according to claim 15, wherein said mixture of water and acetone is a mixture containing 70% to 90% acetone and 10% to 30% water.

17. The method according to claim 6, wherein said solvent or solvent mixture is a mixture of water and propylene glycol.

18. The method according to claim 17, wherein said mixture of water and propylene glycol is a mixture containing 40% to 60% propylene glycol and 40% to 60% water.

19. The method according to claim 6, wherein said solvent or solvent mixture is a mixture of water and butylene glycol.

20. The method according to claim 19, wherein said mixture of water and butylene glycol is a mixture containing 40% to 60% butylene glycol and 40% to 60% water.

21. The method according to claim 1, wherein said composition further contains at least one substance selected from the group consisting of vitamin A and its esters, vitamin A palmitate, vitamin A acetate, vitamin E and its esters, vitamin E phosphate, vitamin E acetate, vitamin C and its derivatives, magnesium ascorbylphosphate, xanthines, caffeine, Asiatic acid, madecassic acid, asiaticosides, madecoassosides, extracts of *Centella asiatica*, ellagic acid, soya saponins, extracts of *Bertholletia*, extracts of *Panax Ginseng*, pure sea water, magnesium aspartate, manganese chloride, cyclic AMP, D-xylose, hyaluronic acid, calcium gluconate, isoflavones, ammonium glycyrrhizinate, corticosteroids, extracts of *Phellodendron amurense*, resveratrol and piceids.

22. The method according to claim 1, wherein said composition contains said extract at a concentration ranging between 0.01 and 10 weight percent.

* * * * *